United States Patent
Nakon

(10) Patent No.: US 9,970,078 B2
(45) Date of Patent: May 15, 2018

(54) METHOD FOR PRODUCING A SOLID SCANDIUM-CONTAINING MATERIAL OF ENHANCED SCANDIUM CONTENT

(71) Applicant: Scandium Pty Ltd, Queensland (AU)

(72) Inventor: David Gregory Nakon, Queensland (AU)

(73) Assignee: Element 21 Pty Limited (AU)

( * ) Notice: Subject to any disclaimer, the term of this patent is extended or adjusted under 35 U.S.C. 154(b) by 338 days.

(21) Appl. No.: 14/650,923

(22) PCT Filed: Dec. 10, 2013

(86) PCT No.: PCT/AU2013/001445
§ 371 (c)(1),
(2) Date: Jun. 10, 2015

(87) PCT Pub. No.: WO2014/094037
PCT Pub. Date: Jun. 26, 2014

(65) Prior Publication Data
US 2015/0368755 A1    Dec. 24, 2015

(30) Foreign Application Priority Data
Dec. 17, 2012    (AU) ................................ 2012905510

(51) Int. Cl.
*C22B 59/00*        (2006.01)
*C22B 3/04*         (2006.01)
(Continued)

(52) U.S. Cl.
CPC ............ *C22B 59/00* (2013.01); *C01F 17/005* (2013.01); *C01F 17/0006* (2013.01);
(Continued)

(58) Field of Classification Search
CPC ....................................................... C22B 59/00
See application file for complete search history.

(56) References Cited

U.S. PATENT DOCUMENTS

| | | | |
|---|---|---|---|
| 4,624,703 A | 11/1986 | Vanderpool et al. |
| 4,650,652 A | 3/1987 | Naitou et al. |

(Continued)

*Primary Examiner* — Melissa S Swain
(74) *Attorney, Agent, or Firm* — Hartman Global IP Law; Gary M. Hartman; Domenica N. S. Hartman

(57) ABSTRACT

A method for producing a solid scandium-containing material comprises providing an aqueous solution containing carbonate ions, carbamate ions, hydrogen carbonate ($HCO_3^+$) ions, or mixtures thereof, contacting the aqueous solution with a scandium containing material containing one or more impurities to produce a scandium-loaded solution and a depleted scandium containing material, separating the depleted scandium containing material from the scandium loaded solution, treating the scandium loaded solution to cause precipitation of a solid scandium-containing material while avoiding or minimizing precipitation of impurities present in the aqueous solution, and separating the solid scandium-containing material from the solution. In another embodiment, a high purity scandium containing is produced by contacting a solid material containing scandium with an acid to form a scandium loaded solution, separating the scandium loaded solution from any solids, adding additional acid to the scandium loaded solution to reduce the pH and precipitating a high purity scandium oxalate material by adding oxalic acid to the solution.

22 Claims, 2 Drawing Sheets

(51) Int. Cl.
*C22B 3/44* (2006.01)
*C01F 17/00* (2006.01)
*C07C 51/41* (2006.01)
*C07F 5/00* (2006.01)
*C22B 7/00* (2006.01)

(52) U.S. Cl.
CPC .......... *C01F 17/0043* (2013.01); *C07C 51/41* (2013.01); *C07F 5/003* (2013.01); *C22B 3/04* (2013.01); *C22B 3/44* (2013.01); *C22B 7/007* (2013.01); *C01P 2006/80* (2013.01); *Y02P 10/234* (2015.11)

(56) References Cited

U.S. PATENT DOCUMENTS

| | | |
|---|---|---|
| 4,808,384 A | 2/1989 | Vanderpool et al. |
| 4,898,719 A | 2/1990 | Rourke et al. |
| 5,039,336 A | 8/1991 | Feuling |
| 5,787,332 A | 7/1998 | Black et al. |
| 2012/0207656 A1 | 8/2012 | Duyvesteyn |

US 9,970,078 B2

METHOD FOR PRODUCING A SOLID SCANDIUM-CONTAINING MATERIAL OF ENHANCED SCANDIUM CONTENT

TECHNICAL FIELD

The present invention relates to a method for producing a solid scandium-containing material of enhanced scandium content.

BACKGROUND ART

Scandium is a high value metal, typically supplied in the form of scandium oxide. Annual world production of scandium is quite small, totalling approximately 10 tonnes per annum. The majority of scandium oxide production takes place in China, where scandium oxide is recovered as a by-product of other material processing activities.

Due to the small annual production of scandium, it is a high value material, with prices for scandium oxides ranging from $1,500 per kilogram to $7,000 per kilogram, depending upon purity.

Scandium is used as an alloying agent in aluminium alloys. Addition of scandium in amounts of up to 0.5% by weight to aluminium alloys can significantly improve the properties of the alloys. These alloys are used in aircraft manufacture, and sporting goods requiring high-strength, such as baseball bats, bicycle frames and bicycle components. Scandium is also finding use as a component used in mixed metal oxides in fuel cells. Scandium is also used in the manufacture of high intensity discharge lamps.

Scandium has typically been produced as a by-product of other metal recovery processes. For example, scandium has been produced from tungsten digestion sludge, uranium tailings, Bayer process red mud, titanium white hydrolytic solution, zircon ore, tantalum residues and niobium residues. Production of scandium products via hydrometallurgical pathways has typically been achieved using three main techniques or combinations of those techniques, these being ion exchange, solvent extraction or multistage precipitation and re-leaching to form an enriched scandium product from a feed solution containing scandium and a host of impurities.

Common final steps in these hydrometallurgical processes involve the production of a scandium hydroxide precipitate, which may be directly calcined to form a final scandium oxide product. Alternatively, the hydroxide may be an intermediate which is subsequently dissolved in acid and precipitated as scandium oxalate by the addition of oxalic acid. A number of earlier processes also use the direct precipitation of scandium oxalate by adding oxalic acid to aqueous strip liquors generated by solvent extraction and ion exchange techniques.

The step of forming scandium oxalate is known to be beneficial for scandium purification. Typically, however, some impurities originally present in the hydroxide or strip liquor also report to the scandium oxalate, thereby decreasing the purity of the final scandium oxide generated by calcination. Regardless of the prior processes employed, impurities tend to report into the final scandium product, thereby making the production of greater than 99.9% pure scandium oxide difficult to obtain.

U.S. Pat. No. 4,988,487, assigned to GTE Laboratories, Inc., describes an ion exchange method for recovering scandium values from industrial waste sludge. In this method, tungsten rich waste sludge is contacted with an acidic solution to dissolve scandium, iron and manganese into the acidic solution. The acidic solution contains a reducing agent such that $Mn^{4+}$ ions are converted to $Mn^{2+}$ ions. Ferric iron ions ($Fe^{3+}$) are converted to ferrous ions ($Fe^{2+}$). The solution is then contacted with an ion exchange resin at a pH of from 1.8 to 2.2, which results in scandium loading onto the ion exchange resin. An important step in this process is the reduction of manganese and iron ions to their respective divalent states, which minimises loading of these impurities onto the ion exchange resin and consequently minimises contamination of the final scandium oxide.

Scandium is subsequently eluted from the loaded resin using a chelating agent (diglycolic acid being a preferred chelating agent), which forms an enriched scandium strip solution. Scandium is then precipitated from the solution by adding ammonium hydroxide to increase the pH to between 7 and 9. This results in the formation of a scandium hydroxide precipitate which, despite the steps of iron and manganese reduction followed by ion exchange, is noted to be of only about 90% purity.

Ditze and Kongolo (1997) describe a process for the recovery of scandium from magnesium, aluminium and iron scraps. After various steps, a scandium loaded liquid organic solvent is formed and subsequently stripped using concentrated caustic soda solution. Stripping concurrently generates a scandium hydroxide precipitate that is separated and calcined to produce an impure scandium oxide product containing 0.5% magnesium and a 0.4% iron.

U.S. Pat. No. 5,787,332, assigned to Fansteel, Inc., describes a multi-stage process for the recovery of tantalum, niobium and scandium from waste residues. In this process, after several upstream leaching and precipitation steps, a scandium loaded liquid organic phase is formed, which is subsequently stripped with hydrofluoric acid solution to generate a strip liquor enriched in scandium. The addition of sodium hydroxide and heat is used to precipitate scandium hydroxide from the scandium enriched solution, noting that impurities including zirconium, titanium and iron are also present in the precipitate.

To assist in removal of these impurities, the precipitate is dissolved in hydrochloric acid, heated and pH adjusted to pH 4 with sodium hydroxide to precipitate zirconium, titanium and iron by hydrolysis. Following removal of these impurities, the scandium solution is treated with oxalic acid to precipitate scandium oxalate, which is filtered and calcined to produce a final scandium oxide product. Despite this process using the purification steps of solvent extraction, impurity hydrolysis and oxalate precipitation, the final scandium oxide does not exceed 99.0% purity.

U.S. Pat. No. 4,898,719, assigned to GTE Laboratories Inc., describes a liquid extraction process for the recovery of scandium. In this process, a digestion solution containing dissolved scandium and other base metals is formed. Dissolved iron is brought to the divalent state by reduction and the pH is reduced to about 2. Scandium is selectively extracted from the solution using an organic extractant consisting of thenoyltrifluoroacetone (TTA) dissolved in an aromatic solvent. The scandium is described as forming a very stable neutral chelate complex with the TTA. The TTA shows a high degree of selectivity for scandium over the divalent transition metals, alkaline earth metals, alkali metals and rare earth metals in the system. Scandium is recovered from the organic phase by stripping with an acid, followed by precipitation of scandium as a hydroxide or oxalate from the acid solution. The precipitation of scandium hydroxide is achieved by the addition of ammonium hydroxide and is noted to generate a product of 80.5% scandium oxide purity after calcination. The precipitation of scandium oxalate is achieved by the addition of oxalic acid and is noted to generate a product of 89% scandium oxide purity after calcination. The production of high purity scandium oxide, such as 99.9% pure scandium oxide, is not achieved, even in light of the use of iron reduction, selective solvent extraction and oxalate precipitation steps.

The present applicant does not concede that the prior discussed in this specification forms part of the common general knowledge in Australia all elsewhere.

Throughout this specification, the word "comprising" and its grammatical equivalents should be taken to have an inclusive meaning unless the context of use indicates otherwise.

SUMMARY OF INVENTION

It is an object of the present invention to provide a method to remove one or more impurities from scandium-containing material prior to the step of forming a scandium oxide product.

In some embodiments, is an object of the present invention to provide a process that will enable the production of scandium oxide of 99.9% purity or greater.

According to a first aspect, the present invention provides a method for producing a solid scandium-containing material comprising the steps of:
a) providing an aqueous solution containing carbonate ions, carbamate ions, hydrogen carbonate ($HCO_3^+$) ions, or mixtures of two or more thereof;
b) contacting the aqueous solution with a scandium containing material containing one or more impurities to transfer scandium into the solution to produce a scandium-loaded solution and a depleted scandium containing material;
c) separating the depleted scandium containing material from the scandium loaded solution;
d) treating the scandium loaded solution to cause precipitation of a solid scandium-containing material whilst avoiding or minimising precipitation of impurities present in the aqueous solution; and
e) separating the solid scandium-containing material formed in step (d) from the solution formed in step (d).

The aqueous solution provided in step (a) may contain ammonium carbonate, ammonium hydrogen carbonate, ammonium carbamate, sodium carbonate, sodium hydrogen carbonate, potassium carbonate or potassium hydrogen carbonate, or mixtures thereof. The aqueous solution provided in step (a) will preferably contain ammonium carbonate, ammonium hydrogen carbonate, or both. The solution will normally be an alkaline solution (i.e. having a pH above 7).

Persons skilled in the art will understand that solutions that contain any one of ammonium carbonate, ammonium hydrogen carbonate or ammonium carbamate will tend to form an equilibrium mixture with the other two salts, thereby resulting in a solution containing mixtures of the three salts. It is for this reason that manufacturers of ammonium carbonate, for instance, will often cite that the reagent (e.g. ammonium carbonate) is a mixture of the three compounds.

It will be appreciated that the aqueous solution provided in step (a) can be of any strength that is practical for use for the application at hand. However, in some preferred embodiments of the present invention, the solution is approximately in the order of 10 wt % strength.

In some embodiments of the present invention, the aqueous solution provided in step (a) has a pH of between 8 and 11, although alkaline solutions having pH outside that range may also be used in some embodiments.

Step (b) involves contacting the aqueous solution with an impure scandium containing material to transfer scandium into the solution and to produce a depleted scandium containing material.

The scandium containing material may comprise a scandium loaded ion-exchange resin, or it may comprise a scandium-loaded liquid organic extractant, or it may comprise a solid scandium containing material such as a residue, waste or intermediate arising from the treatment of an ore or concentrate or arising from the treatment of another solid material.

In some embodiments of the present invention, the scandium-containing material may comprise a scandium hydroxide precipitate containing one or more impurities.

The scandium containing material provided as a feed material to the method of the present invention may include but is not limited to one or more impurities selected from aluminium, calcium, cobalt, chromium, copper, iron, magnesium, manganese, nickel, phosphorus, lead, sulphur, arsenic, antimony, silicon, titanium, zinc and zirconium. The method of the present invention may also be used to separate other impurities from a scandium-containing material.

In step (b), the ratio of aqueous solution to the scandium containing material can encompass any particular ratio that is sufficient for transferring scandium into the solution. The person skilled in the art will readily be able to conduct very simple experimental tests to determine an appropriate ratio.

The temperature at which the step (b) is performed is suitably below 60° C. In particular, if the aqueous solution contains ammonium carbonate, ammonium hydrogen carbonate, ammonium carbamate, or mixtures thereof, the skilled person will understand that the ammonium carbonate, ammonium hydrogen carbonate or ammonium carbamate tend to decompose at elevated temperatures and atmospheric pressure to liberate carbon dioxide and ammonia. This should be avoided in step (b). More preferably, the temperature at which step (b) is performed is suitably below 40° C.

Desirably, the pH of the aqueous solution in step (b) is from 8 to 11.

Transferring of scandium from the impure scandium containing material into the aqueous solution may be achieved by mixing or contacting the aqueous solution with the scandium containing material for a period of time that is sufficient to allow the solution to become enriched with scandium. Typically, scandium ions will be transferred into the solution. Mixing or contacting of the scandium containing material with the solution may occur in a batch manner or a continuous manner. One or more mixing/contacting stages may be used. Co-current, counter current and/or cross current contacting processes may be used.

In some embodiments of the present invention, one or more oxidising agents may be present in the solution. The one or more oxidising agents may be selected so that oxidising agents that are beneficial to a subsequent scandium purification process are used. The one or more oxidising agents may be selected from but not limited to one or more of hydrogen peroxide, potassium permanganate, sodium hypochlorite, calcium hypochlorite, air, oxygen, chlorine, sodium peroxide, sodium persulphate, ozone, and Caro's acid.

The presence of one or more oxidising agents in the solution is particularly useful if the impure scandium containing material contains manganese or iron. At the pH of the solution used in step (b) (for example, from 8 to 11), any manganese or iron that may go into the aqueous solution is oxidised to $Mn^{4+}$ and $Fe^{3+}$, respectively, which tend to precipitate from solution due to hydrolysis. Therefore, manganese and iron are not transferred to any great extent into the loaded scandium containing solution.

In some embodiments of the present invention, one or more reducing agents may also be present in the solution. Reducing agents may be selected so that they are beneficial to the scandium purification process that is used. Reducing agents that may be present in the solution include metabisulphite salts, sulphite salts, sulphide salts, hydrogen sulphide, sulphur dioxide and sulphurous acid. Other common reducing agents may also be used, for example, such as the addition of metallic iron or zinc powder.

Contacting of the impure scandium containing material with the aqueous solution in step (b) may occur under a blanket gas, such as nitrogen or argon. This may be useful, for example, where it is desired to avoid oxidation during the contacting step, or where reducing agents are present in the solution. It will be appreciated that other embodiments of the invention may not require the use of a blanket gas. For example, if oxidation is to be promoted in step (b), a blanket gas may not be required.

Step (c) of the method of the present invention involves separating the scandium loaded solution from the depleted scandium containing material. Any suitable separation technique known to the person skilled in the art may be used. The particular separation technique that is selected will largely depend upon the impure scandium containing material that has been treated. For example, if the scandium containing material is a solid scandium hydroxide, an ion exchange resin, a solid residue, waste or intermediate, the depleted scandium containing material will typically comprise a solid residue. A solid/liquid separation technique may be used to separate the solid residue from the scandium loaded solution. Such techniques may be selected from filtration, centrifugation, settling, clarification, thickening, use of hydrocyclones and the like. In embodiments where the scandium containing material comprises an organic extractant, the organic phase having depleted scandium content that is formed in step (b) may be separated from the scandium loaded solution by settling.

The scandium loaded solution of step (c) will have an enhanced ratio of scandium to impurities when compared to the impure scandium containing material provided to step (b). Indeed, in some embodiments, the scandium loaded solution may have a decreased content (compared to the content of the impure scandium containing material) in respect of one or more of the following impurities: aluminium, calcium, cobalt, chromium, copper, iron, magnesium, manganese, nickel, phosphorus, lead, sulphur, arsenic, antimony, silicon, titanium, zinc and zirconium. It will be appreciated that the method of the present invention should not be considered to be limited to reducing the content of the impurities specifically listed above and the method encompasses the removal or reduction of any impurities, including rare earth metals and rare earths, that may be present in the scandium-containing material.

Step (d) of the present invention involves the precipitation of a solid scandium-containing material. Suitably, the solid scandium-containing material may comprise scandium carbonate, scandium hydrogen carbonate or complexes thereof.

Precipitation of the solid scandium-containing material in step (d) may be achieved by adding one or more acids to the scandium loaded solution. This reduces the pH of the solution to cause precipitation of a solid scandium-containing material. Desirably, the addition of acids is not extended into a pH zone where the scandium-containing solid material begins to re-dissolve due to acid attack. In some embodiments, the pH in step (d) does not go below pH 5. In some embodiments, the pH in step (d) falls within the range of from 5 to 7.5.

Therefore, and somewhat surprisingly, by controlling the acid addition to the scandium loaded solution, it has been found that there exists an acid addition range whereby a scandium-containing solid material can be nearly completely precipitated from the scandium loaded solution. It is believed that the solid scandium containing material that is precipitated in step (d) will comprise a scandium carbonate/scandium hydrogen carbonate containing complex. However, detailed studies by the present applicant to fully characterise the precipitate scandium containing solid have not yet been conducted.

A wide range of acids or combination of acids may be used in step (d). Generally, any acid or combination of acids that is a stronger acid than carbonic acid can be used to precipitate the scandium-containing solid. Suitable acids may be selected from mineral acids and/or organic acids, such as hydrochloric acid, sulphuric acid, sulphurous acid, nitric acid, acetic acid and formic acid. Preferably, hydrochloric acid is used in step (d).

The addition of acid to the loaded scandium solution results in a decrease in the pH of the solution. During this process, carbonate and hydrogen carbonate ions become protonated such that to some extent they decompose into carbon dioxide and water. The amount of acid added will generally control the extent of scandium precipitation from the system. However, as mentioned above, the amount of acid added should not be so great that the solid scandium-containing material that precipitates starts to re-dissolve due to acid attack.

In embodiments where the aqueous solution provided in step (a) comprises ammonium carbonate, ammonium hydrogen carbonate or ammonium carbamate, step (d) may alternatively comprise partial boiling to drive off ammonia and carbon dioxide or steam stripping to drive off ammonia and carbon dioxide. These techniques advantageously lend themselves to collection and recycling of the carbon dioxide and ammonia gases to reform the solution of step (a), if desired. Similarly to embodiments in which acid is added to the scandium loaded solution, many impurities stay in solution during this process, thereby assisting the generation of an enriched scandium containing precipitate having low impurity levels.

Impurities removed or partially removed as a result of step (d) may be selected from, but are not limited to, aluminium, calcium, cobalt, chromium, copper, iron, potassium, magnesium, manganese, sodium, nickel, lead, sulphur, arsenic, antimony, silicon, titanium, zinc and zirconium, or mixtures of two or more thereof.

The process of the present invention provides a number of benefits over prior processes described in literature. For example, Pasechnik et al (2004) described experiments whereby scandium hydroxide is dissolved in solutions containing sodium carbonate and/or sodium hydrogen carbonate. To precipitate scandium from the solutions, caustic soda is added to form a mixture of basic scandium carbonate and a compound noted to be $Na_5Sc(CO_3)_4$. To overcome an unfavourable caustic consumption and precipitation time, the authors further describe achieving the precipitation by the addition of zinc to form a zinc(II)-scandium(III) complex. These scandium precipitation techniques suffer from the drawback of introducing contaminant metal ions (sodium and/or zinc ions) into the system which report into the scandium precipitate, thereby complicating downstream refining to produce high purity in scandium product/s.

D. I. Smirnov and T. V. Molchanova (1997) describe an ion exchange process for the recovery of scandium and uranium from red mud. In this process, a scandium-loaded ion exchange resin is eluted with sodium carbonate solution to form a scandium rich eluate. Similar to the process described by Pasechnik et al, scandium is precipitated from the solution by the addition of an excess of sodium hydroxide to the extent of 20 to 30 g per liter. This process will therefore suffer from the drawbacks mentioned above.

U.S. Pat. Nos. 4,624,703 and 4,808,384, both assigned to GTE Products Corporation, describe processes for the recovery of scandium from tungsten bearing wastes. Common to these specifications is the use of an ammonium carbonate solution to strip scandium from a scandium-loaded organic liquid extractant. Both patents describe the recovery of scandium from the pregnant ammonium carbonate liquor by evaporating the solution to dryness, which incurs the disadvantage that all impurities present in the strip liquor report to the dried scandium precipitate.

The solid scandium-containing material that precipitates in step (d) and is separated from the solution in step (e) may be further processed to produce high purity scandium oxide.

In a second aspect, the present invention provides a method for producing high purity scandium containing material comprising the steps of:
i) contacting a solid material containing scandium with an acid to thereby form a scandium loaded solution,
ii) separating the scandium loaded solution from step (i) from any solids
iii) adding additional acid to the scandium loaded solution from step (ii) to reduce the pH thereof; and
iv) precipitating a high purity scandium oxalate material by adding oxalic acid to the solution from step (iii).

In one embodiment, the scandium containing material may comprise scandium carbonate, scandium hydrogen carbonate, a scandium carbonate complex or a scandium hydrogen carbonate complex, or mixtures of two or more thereof. The scandium containing material is suitably the scandium-containing solid material from step (e) of the first aspect of the present invention.

The method of the second aspect of the present invention may further comprise calcining the high purity scandium oxalate material from step (iv) to form a high purity scandium oxide.

A wide range of acids or combination of strong acids may be used in step (i). Suitable acids may be selected from mineral acids, preferably hydrochloric acid or nitric acid. More preferably, concentrated hydrochloric acid is used in step (i).

Adding hydrochloric acid to the solid material comprising scandium carbonate, scandium hydrogen carbonate, a scandium carbonate complex or a scandium hydrogen carbonate complex, or mixtures of two or more thereof results in scandium being dissolved and carbon dioxide being liberated to produce a scandium chloride containing solution and a solid residue.

In some embodiments, the amount of acid added in step (i) is controlled such that any impurity metal ions that go into solution hydrolyse and precipitate from the solution. To achieve this, the acid addition may be controlled such that the pH of the solution after scandium dissolution is between pH 1.5 and pH 3.5. In some embodiments, acid addition is sufficient to dissolve the scandium complex to form, for instance, a scandium chloride solution if hydrochloric acid is used. In step (i), enough acid is added to dissolve the scandium complex. Some impurities may also go into solution, in particular iron (as ferric), but will hydrolyse and precipitate at the pH being used in step (i).

The mixture of solids and solution formed in step (i), or the solution of step (i), may be allowed to react for a period of time that is sufficient to allow dissolved impurity metal ions to hydrolyse and precipitate. This period of time may vary form minutes to a number of hours. It is believed that a period of time of from 1 hour up to 24 hours should be sufficient to allow for hydrolysis and precipitation of impurity metals such as ferric ions and manganese ions.

As impurity metals have precipitated out of the scandium loaded solution, the subsequent solid/liquid separation step results in the formation of a solution containing dissolved scandium having low to very low impurity levels.

The solution and solids are then separated, for example, by filtration or by use of any other solid/liquid separation technique known to be suitable to the person skilled in the art.

In step (iii) further acid is added to the solution. The further acid may comprise nitric acid or hydrochloric acid, preferably concentrated hydrochloric acid. The further acid is suitably the same as the acid added in step (i). The further acid may be added in an amount such that the pH of the solution is reduced to 1.5 or less, more preferably, to pH 1.0 or less.

The pH of the solution in step (iii) is preferably at a level such that any remaining impurity ions in solution do not hydrolyse and/or precipitate as oxalates during step (iv).

Oxalic acid is added to the solution in step (iv) to produce a high purity scandium oxalate material. Scandium oxalate is known to be very insoluble (stable) and to have a very low solubility product. However, other metal oxides, such as alkali earth oxalates and many base metal oxalates, are less stable than scandium oxalate and therefore tend to dissolve under acidic conditions where scandium oxalate will precipitate. Therefore, by deliberately acidifying the solution prior to scandium oxalate precipitation, a precipitate of high purity may be formed as less stable metal oxalates tend to stay in solution.

The high purity scandium oxalate material can be calcined to form high purity scandium oxide. The high purity scandium oxalate material may comprise 99.9% or greater scandium oxalate.

The solid scandium containing material provided to step (i) may comprise the solid scandium containing material obtained from step (e) of the first aspect of the present invention.

DESCRIPTION OF EMBODIMENTS

It will be appreciated that the drawings have been provided for the purposes of illustrating preferred embodiments of the present invention. Therefore, the skilled person will understand that the present invention should not be considered to be limited solely to the features as shown in the attached drawings.

Figure 1:
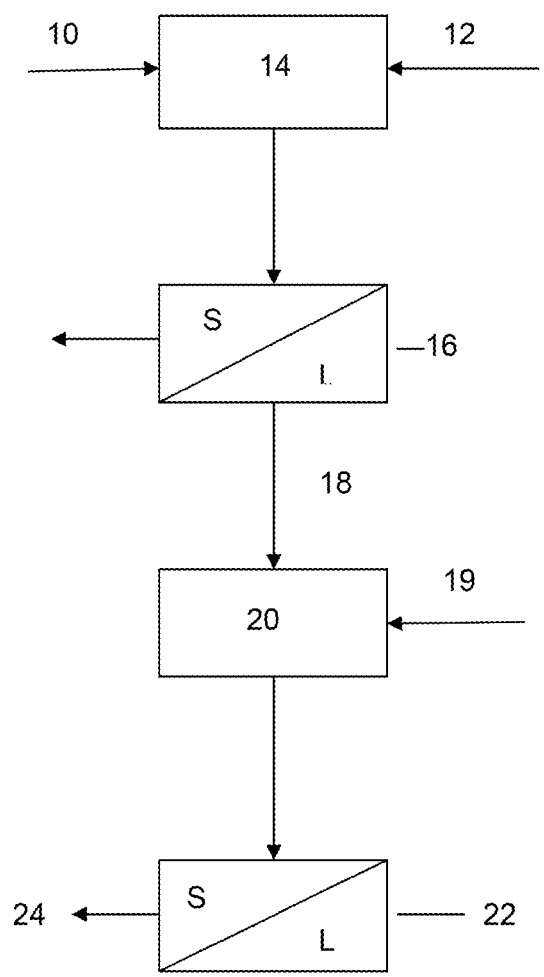
FIG. 1 shows a process flow sheet of an embodiment in accordance with the first aspect of the present invention.

FIG. 1 shows a process flow sheet of an embodiment of the method in accordance with the first aspect of the present invention. In FIG. 1, a scandium containing material 10, which may comprise a scandium hydroxide precipitate that contains one or more impurities, is mixed with an aqueous solution 12 containing ammonium carbonate, ammonium hydrogen carbonate and/or ammonium carbamate. The aqueous solution may comprise 10% ammonium carbonate solution. The solid scandium hydroxide precipitate 10 and the aqueous solution 12 are mixed in a mixing vessel 14. The mixing vessel 14 may comprise a stirred tank or any other mixing apparatus known to be suitable to the person skilled in the art.

Mixing of the impure scandium hydroxide solid and the ammonium carbonate solution in vessel 14 may be conducted at a pH in the range of from about 8 to 11. An oxidising agent, such as permanganate, may also be present so that any manganese that dissolves into solution is oxidised to $Mn^{4+}$ and any iron that dissolves is oxidised to ferric ions. At the pH conditions in vessel 14, $Mn^{4+}$ and ferric ions will not remain in solution to any significant extent and thus the manganese and iron present in the impure scandium hydroxide will largely remain in solid form. Most of the aluminium present in the impure scandium hydroxide will not go into solution and will report to the solid residue, although trace amounts of Al are expected to dissolve. Substantially all of the scandium present in the impure scandium hydroxide will dissolve in the ammonium carbonate solution to produce a scandium loaded solution. This scandium loaded solution may be described as a scandium carbonate solution or liquor.

The scandium loaded solution is separated from the solid residue at the solid/liquid separation step 16. Solid/liquid separation step 16 may comprise a filtration step. The scandium loaded liquor 18 is passed to mixing vessel 20 where the scandium loaded solution is mixed with dilute hydrochloric acid 19. The dilute hydrochloric acid is added in an amount sufficient to decrease the pH to a range of about 5 to 7.5. This results in carbon dioxide being liberated from the solution and a scandium containing solid being precipitated. The scandium containing solid is likely to be one or more of scandium carbonate or scandium hydrogen carbonate, or a scandium carbonate complex or a scandium hydrogen carbonate complex. For convenience, this solid will be referred to as a scandium carbonate precipitate. The ammonium present in the solution will be protonated and will form ammonium chloride in solution. Most of the magnesium, calcium and sodium present in the scandium loaded solution 18 will remain in solution at this pH.

The scandium carbonate precipitate is separated from the solution, for example by filtration, in solid/liquid separation step 22. The scandium carbonate precipitate 24 may optionally be washed with deionised water.

The scandium carbonate precipitate 24 obtained from the process shown in FIG. 1 will have substantially lower impurity levels than the impure scandium hydroxide solid that is supplied to mixing vessel 14.

Figure 2:
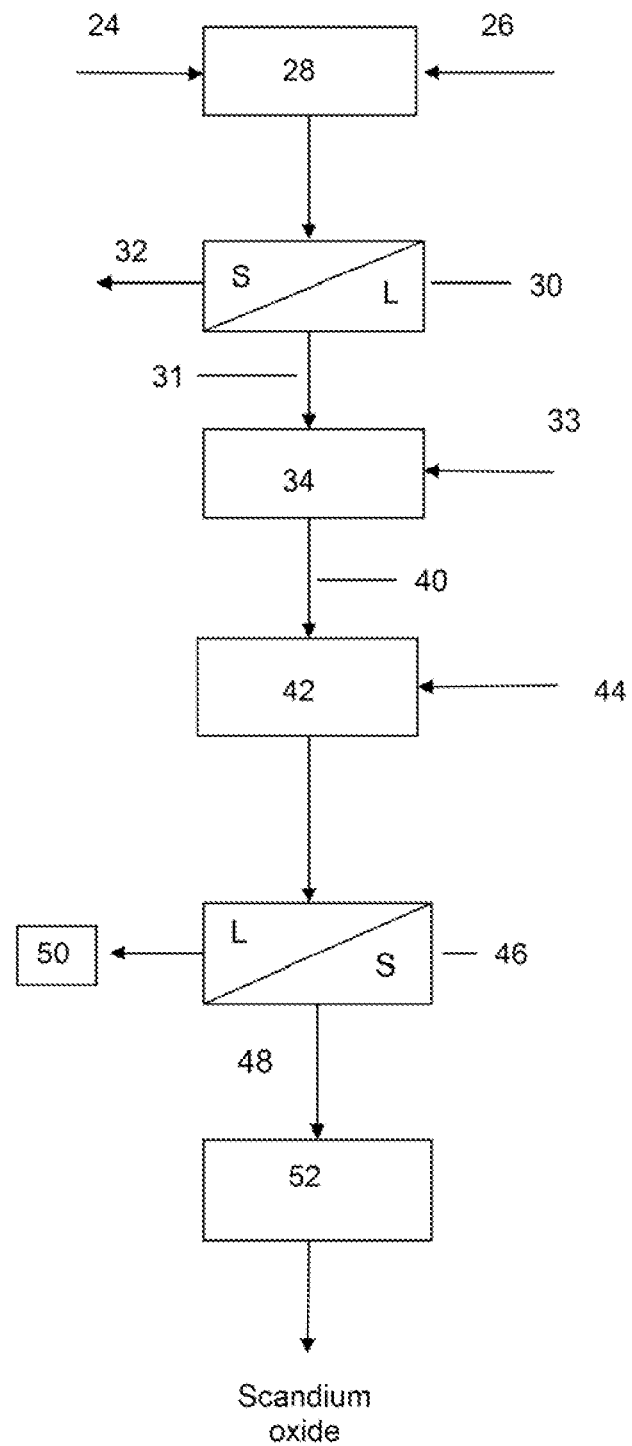
FIG. 2 shows a process flow sheet of an embodiment of a method in accordance with the second aspect of the present invention.

The scandium carbonate precipitate 24 obtained from the process of FIG. 1 may be treated in accordance with the process shown in FIG. 2 to obtain a high purity scandium oxalate material or a high purity scandium oxide. In FIG. 2, the scandium carbonate precipitate 24 is mixed with hydrochloric acid 26 in a mixing vessel 28. The hydrochloric acid 26 may comprise concentrated hydrochloric acid. The pH in vessel 28 is suitably controlled to fall within the range of 1.5 to 3.5. Carbon dioxide is liberated and scandium is dissolved to form a scandium chloride solution. The acidified solution is allowed to react for a period of time ranging from 1 hour to 24 hours so that any iron and manganese that is present in the solution can hydrolysed and precipitate out. A filtration step 30 (or any other solid/liquid separation step) is conducted, with any undissolved solids 32 being discarded. The scandium-loaded solution 31 leaving solid/liquid separation step 30 has a very low impurity level.

Further acid 33 is added to the scandium loaded solution 31 (which is a scandium chloride solution) in step 34. The pH in step 34 may be less than 1.5, or preferably less than 1.0. The scandium chloride solution 40, having a pH of less than 1.5, preferably less than 1.0, is then mixed in mixing vessel 42 with oxalic acid 44. Scandium oxalate seed particles may be added to increase particle size and filterability. Oxalic acid addition is continued until all scandium is precipitated. Any residual impurities (such as magnesium, sodium, iron, manganese, chloride, etc) remain in solution. A solid/liquid separation step 46, which may comprise a filtration step, is used to separate the scandium oxalate solid 48 from the liquid 50

The scandium oxalate solid 48 comprises high purity scandium oxalate. It may be calcined at 52 to produce high purity scandium oxide, such as 99.9% or greater scandium oxide.

The processes shown in FIGS. 1 and 2 may be operated as batch processes.

EXAMPLES

Example 1

The following example demonstrates the production of greater than 99.9% pure scandium oxide from an impure scandium hydroxide feed material. The analytical data displayed in the following tables comes from ICP analysis and although this is very accurate, it does suffer from variances typical to most analytical techniques.

Table 1 displays the approximate composition of the scandium hydroxide feedstock used for the production of the scandium oxide.

TABLE 1

| ICP analysis of impure scandium hydroxide starting material. | | | | | | | | |
|---|---|---|---|---|---|---|---|---|
| | Al | Ca | Co | Cr | Cu | Fe | Mg | Mn | Na |
| Wt % | 0.000 | 0.011 | 0.000 | 0.037 | 0.005 | 0.619 | 0.823 | 0.287 | 1.350 |
| | Ni | P | Pb | S | Sc | Si | Ti | Zn |
| Wt % | 0.001 | 0.005 | 0.000 | 0.063 | 48.600 | 0.047 | 0.004 | 0.033 |

The scandium hydroxide starting material was added to 10 wt % ammonium carbonate solution over an extended period of three hours, with the temperature controlled between 28° C. and 31.5° C. The ratio of solids to liquids was sufficient to dissolve essentially all of the scandium, such that after three hours the scandium concentration in solution was over 6 g per liter. Table 2 shows the concentration of the various components in the solution after 60 minutes contact time and 180 minutes contact time.

TABLE 2

Dissolution of scandium hydroxide material into 10 wt % ammonium carbonate solution, all values in mg/L.

|  | Al | Ca | Co | Cr | Cu | Fe | Mg | Mn | Na |
|---|---|---|---|---|---|---|---|---|---|
| 60 min | <0.1 | 3.0 | <0.1 | 3.0 | 0.3 | 10.0 | 83.0 | 7.9 | 167.0 |
| 180 min | <0.1 | 3.0 | 0.1 | 3.1 | 0.2 | 10.3 | 89.0 | 10.5 | 173.0 |

|  | Ni | P | Pb | S | Sc | Si | Ti | Zn |
|---|---|---|---|---|---|---|---|---|
| 60 min | 0.1 | <5 | 0.2 | 9.0 | 5900 | 3.0 | 0.2 | 3.8 |
| 180 min | 0.1 | <5 | <0.2 | 9.0 | 6200 | 4.0 | 0.2 | 3.4 |

By calculation based upon the complete dissolution of all elements in the starting material, it is demonstrated that significant rejection of impurities has occurred. Worthy of noting are the following elemental percentage rejections of elements dissolved into solution compared to the elements in the starting material: Cr 35.1%, Cu 70.5%, Fe 87%, Mg 15.5%, Mn 71.4%, Ni 21.9%, P 100%, Si 33.1%, Ti 63.7%, Zn 18.5%.

After three hours the system is filtered to remove undissolved impurities. Following this, approximately 540 mL of concentrated (about 222 g per liter) hydrochloric acid solution was added to approximately 3.6 L of the filtered scandium solution. This procedure took place over a period of two hours with mixing, during which evolution of carbon dioxide gas occurred. The temperature remained between 33° C. and 35° C. during this procedure. The pH dropped from pH 9.03 (starting) to pH 7.41 after all the hydrochloric acid had been added. This resulted in the precipitation of a scandium carbonate/hydrogen carbonate containing complex. Samples of the solution were removed at zero minutes, 30 minutes, 60 minutes and 120 minutes from commencement of acid addition. The samples of solution were analysed and the results are given in table 3.

TABLE 3

Solution analysis during precipitation of a scandium carbonate/hydrogen carbonate containing complex by the controlled addition of hydrochloric acid solution (in mg/L).

|  | Al | Ca | Co | Cr | Cu | Fe | Mg | Mn | Na |
|---|---|---|---|---|---|---|---|---|---|
| 0 mins | <0.1 | 3.0 | 0.1 | 3.1 | 0.2 | 10.3 | 89.0 | 10.5 | 173.0 |
| 30 mins | <0.1 | 3.0 | <0.1 | 2.7 | 0.2 | 6.6 | 77.0 | 1.4 | 163.0 |
| 60 mins | <0.1 | Na | <0.1 | 1.8 | 0.3 | 4.8 | 41.0 | <0.1 | 159.0 |
| 120 mins | <0.1 | na | <0.1 | 1.4 | 2.3 | 4.3 | 28.0 | <0.1 | 155.0 |

|  | Ni | P | Pb | S | Sc | Si | Ti | Zn |
|---|---|---|---|---|---|---|---|---|
| 0 mins | 0.1 | <5 | <0.2 | 9.0 | 6220 | 4.0 | 0.2 | 3.4 |
| 30 mins | <0.1 | <5 | <0.2 | 8.0 | 4480 | 3.0 | 0.2 | 3.4 |
| 60 mins | <0.1 | <5 | <0.2 | 7.0 | 857 | 1.0 | 0.3 | 2.2 |
| 120 mins | <0.1 | <5 | <0.2 | 7.0 | 45 | 1.0 | 0.3 | 1.0 |

As shown by Table 3, greater than 99% of the scandium is precipitated from solution by controlled acid addition, with most impurities being rejected to some extent during the process, thereby further assisting the generation of a purified scandium product. Following filtration and washing, the scandium carbonate/hydrogen carbonate containing complex was dried 60° C. and assayed for composition, as displayed in Table 4.

TABLE 4

ICP analysis of the scandium carbonate/hydrogen carbonate containing complex precipitated from solution. Data in the "normalised %" row is adjusted to match the scandium content in the starting scandium hydroxide material. From this, the Delta Wt % and % Rejection of impurities is calculated.

|  | Al | Ca | Co | Cr | Cu | Fe | Mg | Mn | Na |
|---|---|---|---|---|---|---|---|---|---|
| Wt % | 0.000 | 0.000 | 0.000 | 0.007 | 0.001 | 0.017 | 0.259 | 0.039 | 0.020 |
| Normalised % | 0.000 | 0.000 | 0.000 | 0.011 | 0.002 | 0.028 | 0.440 | 0.067 | 0.034 |
| Delta Wt % | 0.000 | 0.011 | 0.000 | 0.026 | 0.003 | 0.590 | 0.383 | 0.221 | 1.316 |
| % Rejection | na | 100.0 | na | 69.4 | 63.7 | 95.4 | 46.5 | 76.8 | 97.5 |

|  | Ni | P | Pb | S | Sc | Si | Ti | Zn |
|---|---|---|---|---|---|---|---|---|
| Wt % | 0.000 | 0.000 | 0.000 | 0.009 | 28.560 | 0.000 | 0.000 | 0.009 |
| Normalised % | 0.000 | 0.000 | 0.000 | 0.015 | 48.600 | 0.000 | 0.000 | 0.016 |
| Delta Wt % | 0.001 | 0.005 | 0.000 | 0.048 | 0.000 | 0.047 | 0.004 | 0.017 |
| % Rejection | 100.0 | 100.0 | na | 75.7 | na | 100.0 | 100.0 | 52.4 |

As can be seen from the data are presented in table 4, most impurity elements have been significantly rejected from the scandium containing solid material.

A final scandium oxide product was subsequently produced following a method in accordance with steps (i) to (iv) outlined above.

Those skilled in the art will appreciate that the present invention may be subject to variations and modifications other than those specifically described. It will be understood that the present invention encompasses all such variations and modifications that fall within its spirit and scope.

The invention claimed is:

1. A method for producing a solid scandium-containing material comprising the steps of:
   a) providing an aqueous solution containing carbonate ions, carbamate ions, hydrogen carbonate ($HCO_3^+$) ions, or mixtures of two or more thereof;
   b) contacting the aqueous solution with a scandium containing material containing one or more impurities to transfer scandium into the aqueous solution to produce a scandium loaded solution and a depleted scandium containing material;
   c) separating the depleted scandium containing material from the scandium loaded solution;

d) treating the scandium loaded solution to cause precipitation of a solid scandium-containing material whilst avoiding or minimising precipitation of impurities present in the scandium loaded solution; and
e) separating the solid scandium-containing material formed in step (d) from the scandium loaded solution formed in step (d).

2. A method as claimed in claim 1 wherein the aqueous solution provided in step (a) contains ammonium carbonate, ammonium hydrogen carbonate, ammonium carbamate, sodium carbonate, sodium hydrogen carbonate, potassium carbonate or potassium hydrogen carbonate, or mixtures thereof.

3. A method as claimed in claim 1 wherein the scandium containing material comprises a scandium loaded ion-exchange resin, or a scandium-loaded liquid organic extractant, or a solid scandium containing material such as a residue, waste or intermediate arising from treatment of an ore or concentrate or arising from treatment of another solid material, or a scandium hydroxide precipitate containing one or more impurities.

4. A method as claimed in claim 1 wherein the pH of the aqueous solution in step (b) is from 8 to 11.

5. A method as claimed in claim 1 wherein one or more oxidising agents are present in the scandium loaded solution.

6. A method as claimed in claim 1 the scandium containing material is a solid scandium hydroxide and the depleted scandium containing material comprises a solid residue, wherein step (c) comprises a solid/liquid separation technique.

7. A method as claimed in claim 1 wherein the solid scandium-containing material formed in step (d) comprises scandium carbonate, scandium hydrogen carbonate or complexes thereof or mixtures of two or more thereof.

8. A method as claimed in claim 1 wherein precipitation of the solid scandium-containing material in step (d) is achieved by adding one or more acids to the scandium loaded solution to reduce the pH of the scandium loaded solution to cause precipitation of a solid scandium-containing material.

9. A method as claimed in claim 8 wherein addition of acid(s) is not extended into a pH zone where the solid scandium-containing material begins to re-dissolve due to acid attack.

10. A method as claimed in claim 9 wherein the pH does not go below 5 in step (d).

11. A method as claimed in claim 1 wherein the aqueous solution provided in step (a) comprises ammonium carbonate, ammonium hydrogen carbonate or ammonium carbamate and step (d) comprises partial boiling to drive off ammonia and carbon dioxide or steam stripping to drive off ammonia and carbon dioxide.

12. A method as claimed in claim 1 further comprising
i) contacting the solid scandium-containing material from step (d) or step (e) with an acid to thereby form a second scandium loaded solution;
ii) separating the second scandium loaded solution from step (i) from any solids;
iii) adding additional acid to the second scandium loaded solution from step (ii) to reduce the pH thereof; and
iv) precipitating a high purity scandium oxalate material by adding oxalic acid to the second scandium loaded solution from step (iii).

13. A method as claimed in claim 12 wherein the solid scandium-containing material comprises scandium carbonate, scandium hydrogen carbonate, a scandium carbonate complex or a scandium hydrogen carbonate complex, or mixtures of two or more thereof.

14. A method as claimed in claim 12 wherein concentrated hydrochloric acid is used in step (i) and the solid scandium-containing material comprises scandium carbonate, scandium hydrogen carbonate, a scandium carbonate complex or a scandium hydrogen carbonate complex, or mixtures of two or more thereof and scandium dissolves and carbon dioxide is liberated to produce a scandium chloride containing solution and a solid residue.

15. A method as claimed in claim 12 wherein the amount of acid added in step (i) is controlled such that impurity metal ions that go into solution hydrolyse and precipitate from the second scandium loaded solution.

16. A method as claimed in claim 15 wherein acid addition in step (i) is controlled such that the pH of the second scandium loaded solution after scandium dissolution is between pH 1.5 and pH 3.5.

17. A method as claimed in claim 15 wherein a mixture of solids and the second scandium loaded solution formed in step (i), or the second scandium loaded solution of step (i), is allowed to react for a period of time that is sufficient to allow dissolved impurity metal ions to hydrolyse and precipitate.

18. A method as claimed in claim 12 wherein the additional acid added to the second scandium loaded solution in step (iii) comprises the same as the acid added in step (i).

19. A method as claimed in claim 12 wherein the additional acid added in step (iii) is added in an amount such that the pH of the second scandium loaded solution is reduced to 1.5 or less, more preferably, to pH 1.0 or less.

20. A method as claimed in claim 12 wherein the high purity scandium oxalate material comprises 99.9% or greater scandium oxalate.

21. A method as claimed in claim 12 wherein the solid scandium-containing material provided to step (i) comprises the solid scandium-containing material obtained from step (e) of the method of claim 1.

22. A method as claimed in claim 12 further comprising calcining the high purity scandium oxalate material from step (iv) to form a high purity scandium oxide.

* * * * *